US00PP32603P2

(12) United States Plant Patent
Griffin

(10) Patent No.: US PP32,603 P2
(45) Date of Patent: Dec. 8, 2020

(54) ***ALOE* PLANT NAMED 'MAUNA KEA'**

(50) Latin Name: ***Aloe* hybrid**
Varietal Denomination: MAUNA KEA

(71) Applicant: Altman Specialty Plants, Inc, Vista, CA (US)

(72) Inventor: Kelly Griffin, Carlsbad, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/873,347

(22) Filed: Mar. 24, 2020

(51) Int. Cl.
*A01H 5/00* (2018.01)

(52) U.S. Cl.
USPC ..... Plt./373

(58) Field of Classification Search
USPC ..... Plt./373
See application file for complete search history.

(56) References Cited

PUBLICATIONS https://www.youtube.com/watch?v=goOigG3X8qg Oct. 28, 2019.*

* cited by examiner

*Primary Examiner* — Annette H Para
(74) *Attorney, Agent, or Firm* — Cassandra Bright

(57) ABSTRACT

A new and distinct cultivar of *Aloe* plant named 'MAUNA KEA' is disclosed, characterized by a star shaped plant with serrated and flanged leaves, white and prominent red protuberances on leaf edges, and red flowers. The new variety is an *Aloe*, typically produced as a garden or container plant.

1 Drawing Sheet

Latin name of the genus and species: *Aloe* hybrid.
Variety denomination: 'MAUNA KEA'.

BACKGROUND OF THE INVENTION

The new cultivar is a product of a planned breeding program. The seed parent is the unpatented *Aloe deltoideodonta Aloe* x 'White Lightning'. The pollen parent is the unpatented *Aloe divaricata* x *Aloe intermedia* x *Aloe* 'White Lightning'. The crossing was made in January 2017 at a commercial greenhouse in Vista, Calif. 'MAUNA KEA' was found and selected by the inventor in June 2017 at the same greenhouse in Vista, Calif.

Asexual reproduction of the new cultivar 'MAUNA KEA' was first performed by tissue culture at a commercial laboratory in Vista, Calif. in July 2017. 'MAUNA KEA' has since produced several generations and has shown that the unique features of this cultivar are stable and reproduced true to type.

SUMMARY OF THE INVENTION

The cultivar 'MAUNA KEA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MAUNA KEA'. These characteristics in combination distinguish 'MAUNA KEA' as a new and distinct *Aloe* cultivar:

1. Leaves serrated and flanged on star shaped plant.
2. White and prominent red protuberances on leaf edges.

3. Red color flower inflorescence.
4. Table top size *Aloe*, maturing at 8" across.

PARENTAL COMPARISON

Plants of the new cultivar 'MAUNA KEA' are similar to the seed parent in most horticultural characteristics. However, plants of the new variety differ from the seed parent in the following:

1. The new variety has a more compact rosette than the seed parent.
2. The new variety has brighter, more colorful leaves than the seed parent.
3. Distinct red and flanged pronounced leaf edge Plants of the new cultivar 'MAUNA KEA' are similar to the pollen parent in most horticultural characteristics. However, plants of the new variety differ in the following:

1. The new variety is a smaller plant than the pollen parent.
2. The new variety produces a more pronounced and brighter red leaf edge.
3. The new variety has a more orderly, attractive star-shaped rosette.

COMMERCIAL COMPARISON

'MAUNA KEA' can be compared to the unpatented commercial variety *Aloe* 'Delta Dawn'. The two *Aloe* varieties are similar in most horticultural characteristics; however, the new variety differs in the following:

1. The new variety is a smaller, more compact plant than this comparator.
2. The new variety has more colorful leaves than this comparator.
3. The new variety has brighter coloring of leaves at all light levels than this comparator.

4. The new variety has a cleaner growth habit than this comparator.

BRIEF DESCRIPTION OF THE PHOTOGRAPH

The accompanying photograph illustrates in full color a typical plant of 'MAUNA KEA' grown in a greenhouse in Vista, Calif. This plant is approximately 24 months old, shown in a 1-gallon container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2007 edition, except where general terms of ordinary dictionary significance are used. The following observations and measurements describe 'MAUNA KEA' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'MAUNA KEA'.

Age of the plant described: 2 years.

PROPAGATION

Time to initiate roots: Approximately 25 days at 22° C.

Root description: Fibrous. Brown, not accurately measured with The R.H.S. Chart.

Propagation method: Tissue culture.

PLANT

Growth habit: Upright rosette, offsetting to form clumps with time.

Container size: 6 inches.

Height: Approximately 20 cm to top of highest leaf. Approximately 52 cm to top of highest inflorescence.

Plant spread: Approximately 285 cm.

Growth rate: Moderate.

Branching characteristics: Offsets from base.

FOLIAGE

Leaf:

*Arrangement*.—Rosette.

*Average length*.—Average 18-20 cm.

*Average width*.—Average 10-14 cm.

*Shape of blade*.—Strongly deltoid.

*Apex*.—Acuminate.

*Base*.—Clasping.

*Margin*.—Flanged and fringed.

*Texture of top surface*.—Bars and ribs.

*Texture of bottom surface*.—Bars and ribs.

*Quantity of leaves per plant*.—Average 10.

*Color*.—Young foliage upper side: Near RHS Green 138C, densely covered with elongated blotches colored near Green-White 157D. Blotches about 2 mm wide and 3 to 7 mm long. Margin near Red 42A. Young foliage under side: Near RHS Green 138C, sparsely covered with elongated blotches colored near Green-White 157D. Blotches about 2 mm wide and 3 to 7 mm long. Margin near Red 42A. Mature foliage upper side: Near RHS Green 138D, densely covered with elongated blotches colored near Green-White 157D. Blotches about 2 mm wide and 3 to 7 mm long. Margin near Red 42B. Mature foliage under side: Near RHS Green 138D, densely covered with elongated blotches colored near Green-White 157D. Blotches about 2 mm wide and 3 to 7 mm long. Margin near Red 42B.

*Venation*.—Linear. Color indistinguishable from leaf blade.

FLOWER

Natural flowering season: Rebloomer, three to four times a year in Southern California.

Inflorescence type and habit: Panicle, seldom branched.

Rate of flower opening: Moderate, successive.

Flower longevity on plant: 1.5 months.

Quantity of flowers: 10 to 20.

Total inflorescence size:

*Height*.—Approximately 30 cm.

*Width*.—Approximately 8 cm.

Corolla:

*Arrangement*.—Perianth cylindrical/corolla small and reflexed.

*Length*.—Approximately 2.5 cm.

*Width*.—Approximately 1 cm at widest point.

*Color*.—Tepals: When opening: Outer surface: Near Red 42A. Inner surface: Near Yellow-Orange 18D. Fully opened: Outer surface: Near Red 42C. Inner surface: Near Yellow-Orange 18D.

Bud:

*Shape*.—Cylindrical.

*Length*.—Approximately 2.5 cm.

*Diameter*.—Approximately 0.5 cm. Color: Near Red 42A.

Pedicels:

*Length*.—Approximately 1 cm.

*Width*.—0.02 cm.

*Aspect*.—Lateral.

*Color*.—Near Red 42D.

Fragrance: None.

REPRODUCTIVE ORGANS

Stamens:

*Number*.—6.

*Filament length*.—Approximately 2.5 cm.

*Filament color*.—Near RHS White 155D.

*Anther length*.—0.25 cm.

*Anther color*.—Near RHS Yellow 7A.

*Anther shape*.—Oval.

*Pollen color*.—Near RHS Yellow 8A.

Pistil:

*Number*.—1.

*Length*.—Approximately 3 cm.

*Style color*.—Near RHS White 155D.

*Stigma*.—Shape: Rounded. Color: Near RHS White 155D. Ovary color: Near RHS Green 138D.

OTHER CHARACTERISTICS

Seeds and fruits: Pods about 10 mm long and 5 mm wide, colored near Green 137D when immature, ripening to Grey-Brown N199D. Seed dust like, colored near Grey-Brown 199C.

Temperature tolerance: Tolerates temperatures from approximately 0° to at least 35° C. Low temperature improved if plants are kept dry.

Disease/pest resistance: Shows mite resistance and black spot resistance.

What is claimed is:

1. A new and distinct cultivar of *Aloe* plant named 'MAUNA KEA' as herein illustrated and described.

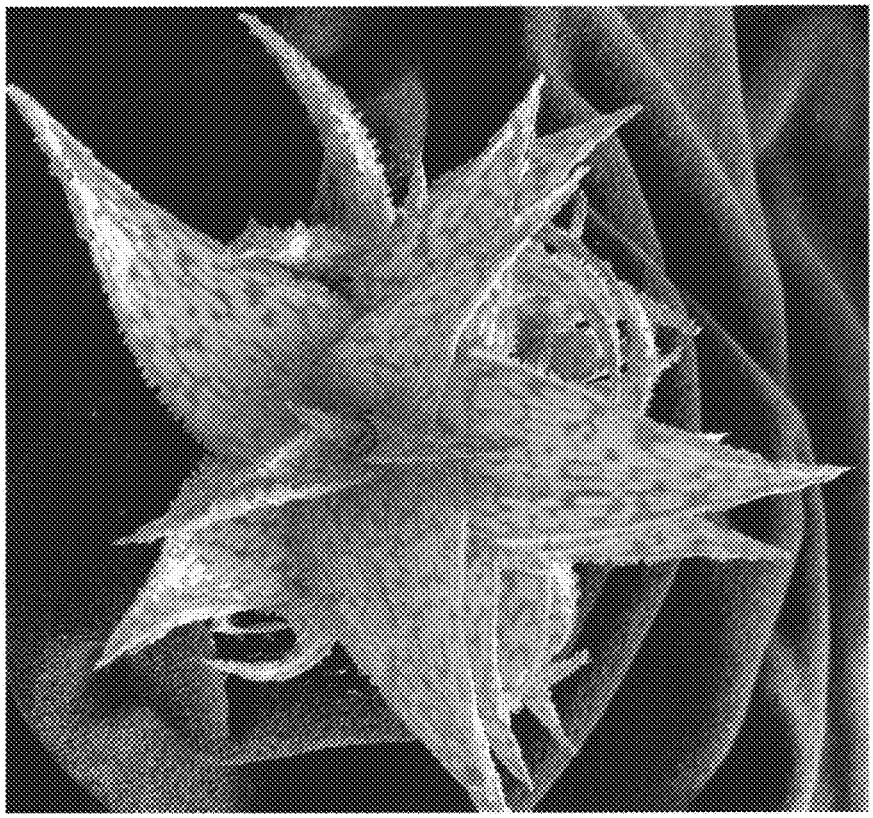

* * * * *